United States Patent [19]

Sipido

[11] Patent Number: 4,471,117

[45] Date of Patent: Sep. 11, 1984

[54] 3,4-DIHYDRO-2H-PYRIMIDO(2,1-B)BENZO-THIAZOLES

[75] Inventor: Victor Sipido, Merksem, Belgium

[73] Assignee: Janssen Pharmaceutica N.V., Beerse, Belgium

[21] Appl. No.: 128,988

[22] Filed: Mar. 10, 1980

Related U.S. Application Data

[63] Continuation-in-part of Ser. No. 50,733, Jun. 21, 1979, abandoned.

[51] Int. Cl.$^3$ ............................................. C07D 513/04
[52] U.S. Cl. .................................... 544/250; 544/247; 424/251
[58] Field of Search ...................... 260/330.3; 544/250, 544/247; 424/251

[56] References Cited

U.S. PATENT DOCUMENTS 4,122,272  10/1978  Acheson et al. ..................... 544/250

OTHER PUBLICATIONS

Rost et al., Khim Ciet. Soed. 4 pp. 495 and 496 (1973) in C. A. 79:18623W.
Singh et al. Ind. J. Chem. 7, pp. 302 and 303 (1969).

Primary Examiner—Richard Raymond
Assistant Examiner—D. B. Springer
Attorney, Agent, or Firm—Geoffrey G. Dellenbaugh

[57] ABSTRACT

This invention relates to 3,4-dihydro-2H-pyrimido[2,1-b]benzothiazoles displaying monoamine-oxidase inhibiting activity. The compounds are useful as antidepressants and anti-Parkinson agents.

4 Claims, No Drawings

3,4-DIHYDRO-2H-PYRIMIDO(2,1-B)BENZO-THIAZOLES

CROSS-REFERENCE TO RELATED APPLICATIONS

This application is a continuation-in-part of our co-pending application Ser. No. 50,733, filed June 21, 1979, abandoned.

BACKGROUND OF THE INVENTION

In U.S.S.R. Pat. No. 366,197, in Khim Geterosikl. Soedin 1973(4), 495 (C.A., 79: 18623w) and in Ind. J. Chem., 1969, 302 there are described a number of 3,4-dihydro-2H-pyrimido[2,1-b]benzothiazoles, certain of which bear a methyl, methoxy, ethoxy or chloro substituent in their 6-, 7- or 8-position and/or a hydroxy or methyl group in their 3-position, said compounds being described as antibacterial agents. The compounds of the present invention differ from said prior art compounds essentially by the nature of the substituents on the 3,4-dihydro-2H-pyrimido[2,1-b]benzothiazole nucleus and by their pharmacological activity.

DESCRIPTION OF THE PREFERRED EMBODIMENTS

This invention is concerned with 3,4-dihydro-2H-pyrimido[2,1-b]benzothiazoles which may structurally be represented by the formula

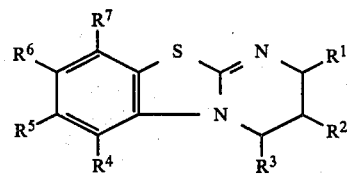
(I-a)

and the pharmaceutically acceptable acid addition salts thereof, the pyrimido[2,1-b]benzothiazolium salts of formula

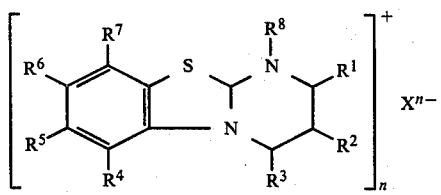
(I-b)

and the non-toxic metal salt complexes thereof, wherein $R^1$, $R^2$ and $R^3$ are each independently selected from the group consisting of hydrogen and aryl;

$R^4$, $R^5$, $R^6$ and $R^7$ are each independently selected from the group consisting of hydrogen, alkyl, lower alkenyl, lower alkynyl, cycloalkyl, trifluoromethyl-lower alkyl, aroyl, α-hydroxyarylmethyl, nitro and a radical of formula, —$NR^9R^{10}$ wherein $R^9$ is a member selected from the group consisting of hydrogen, alkyl, lower alkenyl, lower alkynyl, cycloalkyl, trifluoromethyllower alkyl, lower alkanoyl, lower alkyloxycarbonyl, aryllower alkyl, lower alkyloxylower alkyl, aryloxylower alkyl, hydroxylower alkyl and aminocarbonyl, and $R^{10}$ is a member selected from the group consisting of hydrogen, alkyl, lower alkanoyl, lower alkyloxycarbonyl and a radical of formula —CH=C-(COOalkyl)$_2$ or $R^4$ and $R^5$, $R^5$ and $R^6$ or $R^6$ and $R^7$ may form a tri- or tetramethylene bridge or complete a fused benzene nucleus;

$R^8$ is a member selected from the group consisting of alkyl, lower alkenyl, lower alkynyl and aryllower alkyl;

X is a pharmaceutically acceptable anion; and n represents the valency of the anion;

wherein said aryl is phenyl, optionally substituted with up to 3 substituents, each independently selected from the group consisting of halo, lower alkyl, lower alkyloxy and trifluoromethyl; aroyl is arylcarbonyl; and lower alkanoyl is formyl or lower alkyl carbonyl.

As used in the foregoing and in the following definitions, the term "halo" is generic to fluoro, chloro, bromo and iodo; "lower alkyl" is meant to include straight and branched hydrocarbon radicals having from 1 to 6 carbon atoms such as, for example, methyl, ethyl, 1-methylethyl, 1,1-dimethylethyl, propyl, 1-methylpropyl, 2-methylpropyl, butyl, pentyl, hexyl and the like; "alkyl" is meant to include the above mentioned meaning of "lower alkyl" and the higher homologous having from 7 to 20 carbon atoms such as, for example, heptyl, octyl, nonyl, decyl, undecyl, dodecyl and the like; "lower alkenyl" and "lower alkynyl" are meant to include straight and branched alkenyl, respectively alkynyl, radicals having from 2 to 6 carbon atoms, such as, for example, ethenyl, 2-propenyl, 2-butenyl and the like, and, respectively, ethynyl, 2-propynyl, 2-butynyl and the like; and "cycloalkyl" refers to cyclopropyl, cyclobutyl, cyclopentyl and cyclohexyl.

The anion $X^{n-}$ in the foregoing formula (I-b) may be any pharmaceutically acceptable anion but is preferably an ion arizing from a reactive ester such as, for example, a halide ion, preferably a chloride-, bromide- or iodide ion, or another ion arizing from a reactive ester such as a methanesulfonate or a 4-methylbenzenesulfonate ion. Other pharmaceutically acceptable anions falling within the scope of $X^{n-}$ are, for example, anions arizing from mineral acids, e.g., nitrate, sulfate and phosphate anions, and anions arizing from pharmaceutically acceptable organic acids such as, for example, the anions of acetic-, propanoic- and the like acids.

The compounds of formula (I-a) wherein $R^1$, $R^2$, $R^3$, $R^4$, $R^5$, $R^6$ and $R^7$ are as previously defined, provided that at least one of $R^1$, $R^2$, and $R^3$ is aryl when one of $R^4$, $R^5$, $R^6$ and $R^7$ is methyl while the remaining substituents $R^4$, $R^5$, $R^6$, and $R^7$ are all hydrogen, as well as their pharmaceutically acceptable acid addition salts, their corresponding pyrimido[2,1-b]benzothiazolium salts of formula (I-b), wherein $R^8$, X and n are as above defined, and the metal salt complexes thereof, are deemed to be novel and as useful therapeutic agents herein they constitute an important feature of this invention.

The compounds of formula (I-a) can be derived from an appropriately substituted 3-(2-benzothiazolylamino)-propanol of formula (II) or from an appropriate 2-imino-3(2H)-benzothiazolepropanol of formula (III) by cyclizing said intermediates following art-known cyclizing procedures.

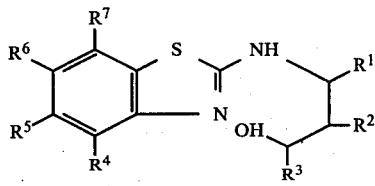

(II)

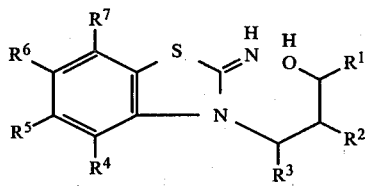

(III)

$R^1$, $R^2$, $R^3$, $R^4$, $R^5$, $R^6$ and $R^7$ are as previously defined.

The above-mentioned cyclization-reactions may be carried out by stirring and heating the intermediates of formula (II) or (III) in an aqueous strong acidic medium such as, for example, aqueous hydrochloric acid, aqueous sulfuric acid and the like, if desired in admixture with a reaction-inert organic solvent such as 1,4-dioxane, tetrahydrofuran and the like.

In order to improve the yields of said cyclization-reactions the hydroxyl function of the intermediates (II) or (III) may be previously converted into a reactive ester residue such as, for example, halo, preferably chloro, bromo or iodo, or a sulfonyloxy group, e.g., methylsulfonyloxy, 4-methylphenylsulfonyloxy and the like, by reacting said alcohols (II) or (III) with an appropriate halogenating agent, e.g., thionyl chloride, phosphor pentabromide and the like, or with an appropriate sulfonating agent, e.g., methylsulfonyl chloride, 4-methylphenylsulfonyl chloride and the like. The thus obtained intermediates are then cyclized by stirring the latter in an appropriate solvent such as, for example, an amide, e.g., N,N-dimethylformamide and the like; dimethylsulfoxide and the like. Somewhat elevated temperatures and the addition of a suitable base such as for example, an alkali metal or an earth alkaline metal carbonate or hydrogen carbonate, e.g., sodium hydrogen carbonate, potassium carbonate and the like, may advantageously be used to enhance the rate of the reaction.

The compounds of formula (I-a) may also be prepared by cyclizing an appropriately substituted 1-aryl-2-mercapto-1,4,5,6-tetrahydro-pyrimidine of formula (IV), wherein L is an appropriate leaving group such as, for example, halo, preferably chloro, bromo or iodo.

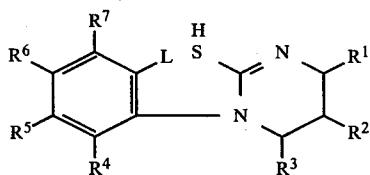

(IV)

$R^1$, $R^2$, $R^3$, $R^4$, $R^5$, $R^6$ and $R^7$ are as previously defined.

Said cyclization-reaction may be carried out following art-known cyclizing procedures generally known in the art, e.g., by stirring and heating the intermediates (IV) in the presence of a suitable reaction-inert solvent, e.g. N,N-dimethylformamide and the like, if desired, in the presence of an appropriate base, e.g., sodium carbonate and the like.

Certain compounds of formula (I-a) may be derived from other appropriately substituted compounds (I-a) by introducing or modifying certain substituent groups according to generally known methods of effecting transformations of functional groups.

Specific examples of functional group transformations which can easily be carried out are as follows:

(i) Nitro-substituted compounds may be prepared by nitrating the corresponding unsubstituted analogs in the usual manner, e.g., by stirring and heating a nitrate salt of the latter in an appropriate strong acidic medium, e.g., aqueous sulfuric acid and the like.

(ii) Nitro-substituted compounds can be converted into the corresponding primary amines according to standard nitro-to-amine reducing procedures, e.g., by catalytically hydrogenating the nitro compound in the presence of an appropriate catalyst, e.g., Raney nickel, palladium-on-charcoal or platinum-on-charcoal.

(iii) Primary amines can in turn be alkylated to produce secondary and tertiary amines following standard N-alkylation procedures. For example, said N-alkylation may be performed by the reaction of the amine with an appropriate reactive ester, e.g. a halide, a methanesulfonate or a 4-methylphenylsulfonate. Otherwise there may be carried out a reductive amination by subjecting a mixture of the amine with an appropriate carbonyl compound in the presence of an appropriate catalyst, e.g. platinum-on-charcoal to a catalytic hydrogenation. Similarly such a reductive amination may also be achieved by reducing a mixture of the amine and an appropriate carboxylic acid with an appropriate reducing agent, e.g., sodium borohydride. In order to prepare secondary amines it may be appropriate to first introduce an appropriate protecting group, thereafter introducing the desired substituent, and finally removing the protecting group. An example of an appropriate protecting group is dialkyl 2-methylenepropanedioate radical, which may easily be introduced by the reaction of the amine with a diaryl 2-(lower alkyloxymethylene)-propanedioate, and which may easily be removed by acid hydrolysis, e.g. in aqueous hydrochloric acid.

(iv) Alkanoylamino-substituted compounds can be prepared by acylating the corresponding amine in the usual manner with an appropriate acylating agent, e.g. an acyl halide or acid anhydride. In order to prepare formylamino-substituted compounds their may be used formaldehyde and N,N-dimethylformamide as acylating agents.

(v) Compounds bearing an aminocarbonylamino substituent can be prepared by reacting the corresponding amine with an appropriate alkali or earth alkaline metal cyanate, e.g. potassium cyanate and the like.

(vi) Hydroxylower alkylamino-substituted compounds may be derived from the corresponding lower alkyl and arylethers by treating the latter with a strong non-oxidizing acid, e.g. hydrobromic acid in acetic acid or, in case of the benzylethers, by catalytically hydrogenolyzing said benzylethers.

(vii) Compounds bearing an α-hydroxyarylmethyl substituent can be derived from the corresponding aroylsubstituted analogs by reducing the carbonyl group of the latter using an appropriate reducing agent, such as, sodium borohydride and the like.

The compounds of formula (I-a) may conveniently be converted into their quaternary ammonium salts of formula (I-b) by reacting a compound of formula (I-a)

with a reagent of formula (V) wherein $R^8$ is as previously defined and Z is a reactive ester group such as, for example, halo, e.g., chloro, bromo or iodo, or a sulfonyloxy group, e.g., methylsulfonyloxy, 4-methylphenylsulfonyloxy and the like, and, if desired, subsequently exchanging the anion Z of the thus obtained compound of formula (I-c) for another therapeutically acceptable anion X, having n as valency.

(V)

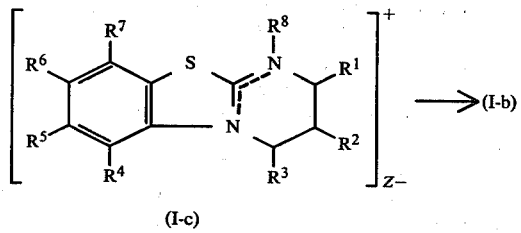

(I-c)

The reaction of (I-a) with (V) is conveniently carried out by stirring and heating the reactants together in the presence of a suitable reaction-inert soluble such as, for example, a nitrile, e.g., acetonitrile, benzonitrile and the like; halogenated hydrocarbons, e.g., dichloromethane; and other common solvents including N,N-dimethylformamide and the like. Most preferably, the reaction is carried out at the reflux temperature of the reaction mixture.

The anion-exchange reaction may be accomplished following art-known methods such as, for example, by treating a compound of formula (I-c) with a large molar excess of an acid corresponding to the anion of the desired salt, or, more preferably, by bringing the salt of formula (I-c) into contact with an ion-exchange resin, which is saturated with the desired anion, and subsequently eluting the desired salt (I-b) from the resin with a suitable relatively polar solvent, or by first converting the salt (I-c) into the corresponding hydroxide and subsequently reacting the latter with an acid corresponding to the anion of the desired salt. The salt (I-c) can be converted into the corresponding hydroxide, e.g., by its reaction with a base or by contacting said salt with an ion-exchange resin, which is saturated with hydroxide ions, and eluting the thus obtained hydroxide from the ion-exchange resin with a suitable relatively polar solvent.

Metal salt complexes of compounds of formula (I-a) may be obtained by the complexation of the latter with an organic or inorganic transition metal salt, such as, for example, halides, nitrates, sulfates, phosphates, (Z)-butenedioates and the like of copper, manganese, zinc, iron and the like transition metals, wherein said transition metals may have any of their naturally existing valencies.

In practice, stoichiometrically defined metal salt complexes may be prepared by dissolving a compound of formula (I-a) in a water-miscible solvent such as, for example, warm ethanol, methanol, 1,4-dioxane or N,N-dimethylformamide, and adding thereto an aqueous solution of the desired metal salts such as, for example, CuSO$_4$; 5H$_2$O, Mn(NO$_3$)$_2$.4H$_2$O, FeCl$_3$.6H$_2$O and the like.

A number of the intermediates used in the foregoing preparations are known compounds, others may be prepared according to art-known methodologies of preparing similar compounds and some of them are novel and consequently their preparation will be described hereafter.

The intermediates of formula (II) may be prepared by cyclizing an appropriately substituted thiourea (VI) wherein Y represents hydrogen or a reactive leaving group such as, for example, halo, e.g., chloro, bromo or iodo, following art-known procedures.

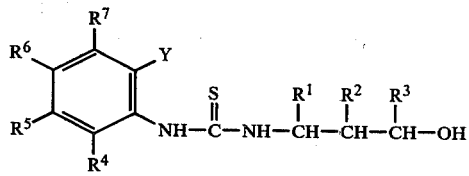

(VI)

$$\xrightarrow{\text{cyclization}} \text{(II)}$$

In case Y is a reactive leaving group the cyclization-reaction can be carried out by stirring and heating the thiourea (VI) in a suitable reaction-inert organic solvent, e.g., N,N-dimethylformamide and the like, preferably, in the presence of an appropriate base, such as an alkali metal or an earth alkaline metal carbonate or hydrogen carbonate or an alkali metal hydride, e.g., sodium carbonate, sodium hydride and the like. In case Y is hydrogen said cyclization may be carried out by stirring and heating the thiourea (VI) in a suitable reaction-inert solvent, e.g. trichloromethane, glacial acetic acid and the like, in the presence of a suitable halogenating agent, e.g., bromide and the like. The latter procedure may yield directly the corresponding compound of formula (I) when at least one of $R^3$ and $R^4$ is a sufficiently electronegative group such as, for example, an aryl group.

The intermediates of formula (VI), used as starting materials herein, can be prepared by reacting an appropriate arylisothiocyanate (VII) with an appropriately substituted 2-aminoethanol (VIII). In the following reaction equation $R^1$, $R^2$, $R^3$, $R^4$, $R^5$, $R^6$ and $R^7$ are as previously defined.

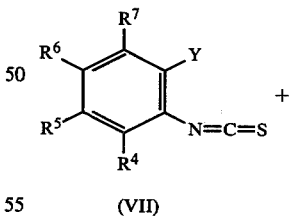

(VII)

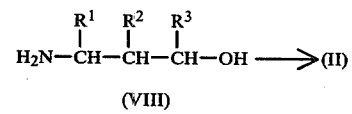

(VIII)

Said reaction is carried out by stirring and, if desired, heating the reactants together in the presence of a suitable reaction-inert solvent such as, for example, a lower alkanol, e.g., ethanol, 2-propanol and the like.

The isothiocyanates (VII), used as starting materials herein can be prepared following art-known methods of preparing such or similar products.

The intermediates of formula (III) can be prepared by N-alkylating an appropriately substituted 2-aminobenzothiazole (IX) with an appropriate alcohol (X) following art-known N-alkylating procedures, i.e., by stirring and, if desired, heating the reactants together in the presence of a reaction-inert solvent such as, for example, a nitrile, e.g., acetonitrile and the like. In the following reaction equation $R^1$, $R^2$, $R^3$, $R^4$, $R^5$, $R^6$ and $R^7$ are as previously defined and W represents a reactive ester residue such as, for example, halo, preferably chloro, bromo or iodo, or a sulfonyloxy group, e.g., methylsulfonyloxy, 4-methylphenylsulfonyloxy and the like.

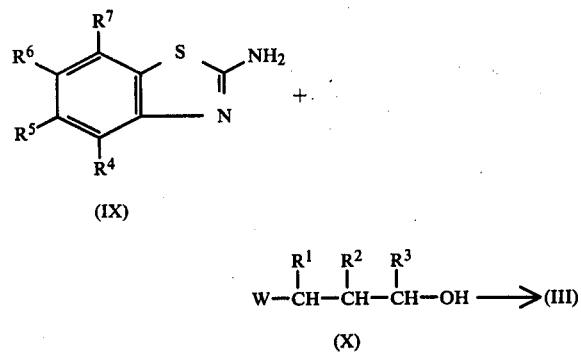

The intermediates of formula (III) wherein $R^3$ is aryl, (III-a), are preferably prepared by the reaction of (IX) with an appropriate carbonyl compound of the formula (XI), yielding an intermediate of formula (XII), and subsequently reducing the latter with an appropriate reducing agent, e.g., sodium borohydride and the like. The reaction of (IX) with (XI) may be carried out following the procedure described hereabove for the reaction of (IX) with (X).

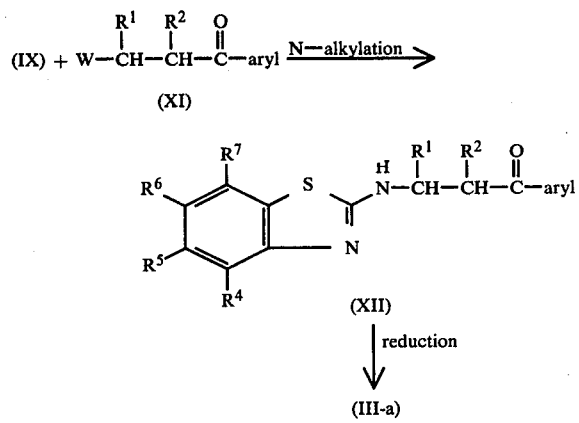

It is obvious that the compounds of formula (I) wherein $R^1$ is other than $R^2$ and/or $R^3$ is other than $R^4$ and/or $R^5$ is other than $R^6$ have at least one asymmetric carbon atom and, consequently, said compounds may exist under different enantiomeric forms. Pure enantiomeric forms of the compounds (I) may be obtained by the application of art-known procedures such as, for example, separation of their diastereomeric salts with optically active acids and the like procedures. Isomers of compounds of formula (I) are naturally intended to be embraced within the scope of this invention.

The compounds of formula (I) have basic properties and thus may be converted to their therapeutically useful acid addition salts by reaction with an appropriate acid, for example, an inorganic such as hydrohalic acid, i.e., hydrochloric, hydrobromic or hydroiodic acid; sulfuric, nitric or thiocyanic acid; a phosphoric acid; and organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic benzoic, 3-phenyl-3-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g. by reaction with alkali such as sodium or potassium hydroxide.

The compounds within the scope of this invention display valuable monoamine oxidase (M.A.O.) inhibiting properties. Monoamine oxidase has been classified into two types A and B which can be differentiated according to their substrate specificity and inhibitor sensitivity. In rat brain, for instance, tryptamine is oxidatively deaminated by the type A enzyme while β-phenylethylamine is preferentially catabolized by the type B enzyme.

The potencies of compounds of formula (I) as M.A.O. inhibitors were determined in an in-vitro experiment as described below.

PREPARATION OF THE MONOAMINE OXIDASE EXTRACT

Male Wistar rats, weighing 150 to 200 g, are killed by decapitation. Brain and other tissues are quickly removed and homogenized in an ice cold 0.25 M sucrose solution with a homogenizer. The total homogenate is centrifuged at low speed (7000 g-min) in a refrigerated centrifuge. The supernatant is stored at 0° C. and the sediment, which contains cell nuclei, unbroken cells and debris, is rehomogenized in an ice cold 0.25 M sucrose solution and centrifuged again at 7000 g-min. The thus obtained supernatants are combined to yield the monoamine oxidase extract.

DESCRIPTION OF THE IN-VITRO EXPERIMENTS

A mixture, containing 0.5 mmoles of [$^{14}$C]tryptamine (specific activity: 50.34 mCi/mmole) or 0.5 mmoles of [$^{14}$C]-phenylethylamine hydrochloride (specific activity: 50.98 mCi/mmole), 113 mmoles of potassium phosphate (pH 7.4), the substance to test and 100 μl of the hereabove described monoamine oxidase extract in a total volume of 0.5 ml, is incubated at 37° C. for 20 minutes. The reaction is stopped by adding 0.2 ml of 2N HCl and the reaction product is extracted in 6 ml of methylbenzene. 4 ml of the organic phase is counted for the radioactivity in a liquid scintillation spectrometer.

The data listed in tables 1 and 2 represent the concentrations of the tested compounds which inhibit 50% of the monoamine oxidase activity, using tryptamine, respectively β-phenylethylamine as substrate. The compounds listed in the tables are not given for the purpose of limiting the invention thereto but in order to exemplify the M.A.O. inhibitory activities of the compounds within the scope of formula (I).

TABLE 1

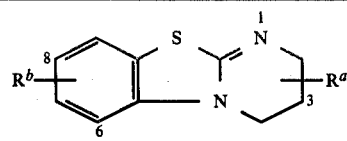

| $R^a$ | $R^b$ | I.C.$_{50}$-value using as substrate in mole/liter: | |
|---|---|---|---|
| | | [$^{14}$C]tryptamine | [$^{14}$C]phenylethylamine.HCl |
| — | 7-C$_3$H$_7$ | $2 \times 10^{-8}$ | $1.2 \times 10^{-6}$ |
| — | 8-C$_4$H$_9$ | $3.2 \times 10^{-8}$ | $2.6 \times 10^{-7}$ |
| — | 6-CH$_3$, 9-C(CH$_3$)$_3$ | $6.5 \times 10^{-8}$ | $>10^{-4}$ |
| — | 9-NH$_2$ | $3.5 \times 10^{-7}$ | $9 \times 10^{-5}$ |
| — | 9-NH—C$_2$H$_5$ | $3 \times 10^{-9}$ | $10^{-4}$ |
| — | 8-NH—i.C$_3$H$_7$ | $9 \times 10^{-8}$ | $2 \times 10^{-5}$ |
| — | 7-NH—CH(C$_2$H$_5$)$_2$ | $3.4 \times 10^{-9}$ | $3.05 \times 10^{-7}$ |
| — | 7-NH—CH$_2$(4-OCH$_3$—C$_6$H$_4$) | $2.5 \times 10^{-7}$ | $6.5 \times 10^{-8}$ |
| — | 8-NH—CH$_2$(4-CH$_3$—C$_6$H$_4$) | $10^{-6}$ | $2 \times 10^{-8}$ |
| — | 8-NH—CH$_2$[3,4,5-(OCH$_3$)$_3$—C$_6$H$_2$] | $2 \times 10^{-5}$ | $3.4 \times 10^{-8}$ |
| — | 7-NH—c.C$_5$H$_9$ | $5 \times 10^{-9}$ | $1.2 \times 10^{-7}$ |
| — | 7-NH—CO—NH$_2$ | $8.5 \times 10^{-7}$ | $1.2 \times 10^{-5}$ |
| — | 8-NH—CH=C(COOEt)$_2$ | $2 \times 10^{-5}$ | $1.6 \times 10^{-7}$ |
| — | 8-c.C$_6$H$_{11}$ | $8.5 \times 10^{-9}$ | $5 \times 10^{-8}$ |
| — | 7-CO—C$_6$H$_5$ | $1.2 \times 10^{-7}$ | $2.5 \times 10^{-6}$ |
| — | 7,8-(CH=CH—CH=CH) | $3 \times 10^{-8}$ | $9 \times 10^{-6}$ |

TABLE 2

| Compound | I.C.$_{50}$-value using as substrate in mole/liter | |
|---|---|---|
| | [$^{14}$C]tryptamine | [$^{14}$C]phenylethylamine.HCl |
| [structure with i.C$_3$H$_7$HN—, C$_2$H$_5$ on N]$^+$ I$^-$ | $1.1 \times 10^{-8}$ | $4.5 \times 10^{-5}$ |
| [structure with C$_9$H$_{19}$—, CH$_2$—CH=CH$_2$ on N]$^+$ Br$^-$ | $2.5 \times 10^{-7}$ | $3.8 \times 10^{-7}$ |

As can be seen from the data listed in tables 1 and 2, certain compounds within the scope of the present invention inhibit the enzyme activity at very low concentration when tryptamine is used as substrate, while a much higher concentration is required to elicit an inhibiting effect when a phenylethylamine substrate is used. Such compounds are preferably monoamine oxidase inhibitors of the type A. On the other hand certain compounds have better inhibiting properties when β-phenylethylamine is used as substrate and, obviously, such compounds have more monoamine oxidase properties of the type B.

As is generally known, compounds which are M.A.O.-inhibitors of the type A can be used as antidepressants while M.A.O.-inhibitors of the B-type can be used as anti-Parkinson agents. Since both types of activity are present in the subject compounds they can theoretically be used in both applications. However, it is obvious that compounds with prevailing M.A.O.-type A inhibiting activity are especially suited as antidepressants while those with prevailing M.A.O.-type B inhibiting properties are particularly useful as anti-Parkinson agents.

In view of the useful antidepressant and anti-Parkinson activity of the subject compounds of formula (I) this invention provides valuable pharmaceutical compositions comprising a compound of formula (I) or a pharmaceutically acceptable acid addition salt or a metal salt complex thereof in an amount which is effective to treat depression and/or Parkinsonism, as the active ingredient, in a solvent or a solid, semi-solid or liquid diluent or carrier. Further it provides an effective method of treating depression, respectively Parkinsonism by administering to the patient an amount of a compound of formula (I) which is effective in the relevant circumstances. Obviously, the compounds of formula (I) may optionally be used in combination with other therapeutically active substances. Pharmaceutical compositions comprising a compound of the formula (I) as the active ingredient may be readily prepared according to conventional pharmaceutical techniques for the usual routes of administration.

Preferred compositions are in unit dosage form, comprising per dosage unit an effective quantity of the active ingredient in admixture with suitable carriers. Although the amount of the active ingredient per unit dosage may vary within rather wide limits, dosage units comprising from about 1 mg to about 500 mg and more particularly from about 5 mg to about 200 mg of the active ingredient are preferred.

The following examples are intended to illustrate and not to limit the scope of the present invention.

PREPARATION OF INTERMEDIATES

Example I

To a stirred and cooled (0°–5° C.) mixture of 110 parts of concentrated nitric acid solution and 314 parts of concentrated sulfuric acid solution are added dropwise 60 parts of 1,2-dichloro-4-nonylbenzene. Upon completion, stirring is continued for 30 minutes at 0° C. The reaction mixture is poured onto crushed ice and the product is extracted with 2,2'-oxybispropane. The extract is washed successively with water and a sodium hydrogen carbonate solution, dried, filtered and evaporated, yielding 70 parts (100%) of 1,2-dichloro-4-nitro-5-nonylbenzene as an oily residue.

Example II

To a stirred and refluxing mixture of 11.2 parts of iron, 100 parts of ammonium chloride solution 0.8N and 20 parts of methylbenzene are added 10.5 parts of (4-chloro-3-nitrophenyl)phenylmethanone and the whole is further stirred at reflux temperature for one hour. Methylbenzene (80 parts) is added and the whole is filtered over Hyflo. The organic layer is separated, dried, filtered and evaporated. The residue is washed with cyclohexane, yielding 8.4 parts of (3-amino-4-chlorophenyl)phenylmethanone; mp. 91.9° C.

Example III

A mixture of 120 parts of 1,2-dichloro-4-nitro-5-nonylbenzene, 2 parts of zinc chloride solution, 83 parts of sodium acetate and 480 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. The residue is dissolved in water and the solution is alkalized with ammonium hydroxide. The product is extracted with 2,2'-oxybispropane. The extract is washed with water, dried, filtered and evaporated. The residue is distilled, yielding 59 parts of 2-nonylbenzenamine; bp. 131°–132° C. at 0.2 mm. pressure.

Example IV

A mixture of 34 parts of 1-(4-methyl-3-nitrophenyl)-1-butanone, 24 parts of 2-propanol saturated with hydrochloric acid and 400 parts of methanol is hydrogenated at normal pressure and at room temperature with 5 parts of palladium-on-charcoal catalyst 10%. After the calculated amount of hydrogen is taken up, the catalyst is filtered off and the filtrate is evaporated. Water is added to the residue and the whole is alkalized with ammonium hydroxide. The product is extracted with 2,2'-oxybispropane. The extract is dried, filtered and evaporated, yielding 25.5 parts of 5-butyl-2-methylbenzenamine as a residue.

Example V

A mixture of 50 parts of 2-chloro-5-nitrobenzenamine, 33.4 parts of methanethial and 450 parts of 1,4-dioxane is stirred and refluxed for 4 hours. The reaction mixture is evaporated, yielding 62.2 parts of 1-chloro-2-isothiocyanato-4-nitrobenzene as a residue.

Example VI

A mixture of 17 parts of (3-amino-4-chlorophenyl)phenylmethanone, 9.5 parts of carbonothioic dichloride and 200 parts of 1,4-dioxane is stirred and refluxed for 15 minutes. The reaction mixture is evaporated and the oily residue is crystallized from 2,2'-oxybispropane. The product is filtered off and dried, yielding 17 parts (85%) of (4-chloro-3-isothiocyanatophenyl)phenylmethanone; mp. 96.7° C.

In a similar manner there are also prepared:
1-isothiocyanato-2-nonylbenzene as a residue;
4-butyl-2-isothiocyanato-1-methylbenzene as a residue; and
2-chloro-1-isothiocyanato-3-nitrobenzene as a residue.

Example VII

To a stirred solution of 24 parts of 1-chloro-2-isothiocyanato-4-nitrobenzene in 200 parts of ethanol 95% are added dropwise 9 parts of 3-amino-1-propanol at a temperature below 20° C. Upon completion, stirring is continued for 30 minutes at room temperature. The reaction mixture is evaporated. The residue is crystallized from acetonitrile. The product is filtered off and dried, yielding 23 parts (72%) of N-(2-chloro-5-nitrophenyl)-N'-(3-hydroxypropyl)thiourea; mp. 126.8° C.

Following the same procedure and using equivalent amounts of the appropriate isothiocyanate and 3-aminopropanol there are also prepared:

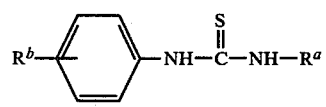

| $R^a$ | $R^b$ | Salt/base | Melting point in °C. |
|---|---|---|---|
| —CH$_2$—CH(C$_6$H$_5$)—CH$_2$OH | 2-Cl, 5-NO$_2$ | — | 160.0 |
| —CH$_2$—CH$_2$—CH$_2$OH | 2-Cl, 5-COC$_6$H$_5$ | — | 110.6 |
| —CH$_2$—CH$_2$—CH$_2$OH | 2,3-(CH$_2$)$_4$ | ½H$_2$O | 116.2 |
| —CH$_2$—CH$_2$—CH$_2$OH | 2-CH$_3$ | — | — |
| —CH$_2$—CH$_2$—CH$_2$OH | 4-C$_2$H$_5$ | — | — |
| —CH$_2$—CH$_2$—CH$_2$OH | 3-C$_3$H$_7$ | — | 100.0 |
| —CH$_2$—CH$_2$—CH$_2$OH | 3-CH$_3$ | — | — |
| —CH$_2$—CH$_2$—CH$_2$OH | 3,4-(CH$_3$)$_2$ | — | 132.2 |
| —CH$_2$—CH$_2$—CH$_2$OH | 4-CH(CH$_3$)$_2$ | — | — |

-continued

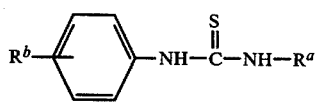

| $R^a$ | $R^b$ | Salt/base | Melting point in °C. |
|---|---|---|---|
| —CH₂—CH₂—CH₂OH | 3-C₄H₉ | — | — |
| —CH₂—CH₂—CH₂OH | 2,3-(CH=CH—CH=CH) | — | 74.0 |
| —CH₂—CH₂—CH₂OH | 2-C₉H₁₉ | — | — |
| —CH₂—CH₂—CH₂OH | 2-C₄H₉ | — | — |
| —CH₂—CH₂—CH₂OH | 3,4-(CH=CH—CH=CH) | — | 127.1 |
| —CH₂—CH₂—CH₂OH | 4-C(CH₃)₃ | — | 110.0 |
| —CH₂—CH₂—CH₂OH | 2-CH₃, 5-CH(CH₃)₂ | — | — |
| —CH₂—CH₂—CH₂OH | 4-C₄H₉ | — | — |
| —CH₂—CH₂—CH₂OH | 2-C₂H₅ | — | — |
| —CH₂—CH₂—CH₂OH | 4-C₃H₇ | — | — |
| —CH₂—CH₂—CH₂OH | 3-C₅H₁₁ | — | — |
| —CH₂—CH₂—CH₂OH | 2,5-(CH₃)₂ | — | — |
| —CH₂—CH₂—CH₂OH | 2-CH₃, 5-C(CH₃)₃ | — | — |
| —CH₂—CH₂—CH₂OH | 4-CH₃ | — | — |
| —CH₂—CH₂—CH₂OH | 2-CH₃, 5-C₄H₉ | — | — |
| —CH₂—CH₂—CH₂OH | 2-Cl, 3-NO₂, 5-C(CH₃)₃ | — | 192.0 |
| —CH₂—CH₂—CH₂OH | 2-Cl, 3-NO₂ | — | 191.1 |

Example VIII

A mixture of 21 parts of N-(2-chloro-5-nitrophenyl)-N'-(3-hydroxypropyl)thiourea, 10 parts of potassium carbonate and 180 parts of N,N-dimethylformamide is stirred and refluxed for 30 minutes. After cooling, 300 parts of water are added and the product is allowed to crystallize. It is filtered off and washed with water, yielding 13.3 parts (72.2%) of 3-[(5-nitro-2-benzothiazolyl)amino]-1-propanol; mp. 140°–144° C.

In a similar manner there are also prepared:

β-[(5-nitro-2-benzothiazolyl)amino]methyl benzeneethanol;

3-{[5-(1,1-dimethylethyl)-7-nitro-2-benzothiazolylamino]}-1-propanol; mp. 153.1° C.; and 3-[(7-nitro-2-benzothiazolyl)amino]-1-propanol; mp. 154° C.

Example IX

A mixture of 14 parts of N-(5-benzoyl-2-chlorophenyl)-N'-(3-hydroxypropyl)thiourea, 5 parts of sodium hydride dispersion 75% and 180 parts of N,N-dimethylacetamide is stirred and heated quickly to 130° C. The reaction mixture is cooled and poured onto water. The precipitated product is filtered off and crystallized from ethanol, yielding 1.8 parts of {2-[(3-hydroxypropyl)amino]-5-benzothiazolyl}phenylmethanone; mp. 162° C.

Example X

To a stirred mixture of 27.7 parts of N-(3-hydroxypropyl)-N'-(3-propylphenyl)thiourea and 240 parts of tetrachloromethane are added 17.6 parts of bromine and the whole is stirred and refluxed for 1 hours. About 80 parts of acetonitrile are added and the formed hydrobromide salt is allowed to crystallize. It is filtered off, washed with acetonitrile and dissolved in water. The free base is liberated in the conventional manner with ammonium hydroxide and extracted with 1,1'-oxybisethane. The extract is dried, filtered and evaporated, yielding 18 parts of 3-(5-propyl-2-benzothiazolylamino)-1-propanol as an oily residue.

Following the same cyclizing procedure there are also prepared:

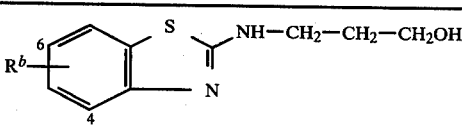

| $R^b$ | Salt/base | Melting point in °C. |
|---|---|---|
| 4,5-(CH₂)₄ | — | 141.0 |
| 4-CH₃ | HBr | 199.2 |
| 6-C₂H₅ | — | 131.6 |
| 5-CH₃ | — | 120.0 |
| 6-CH(CH₃)₂ | HBr | 144.0 |
| 5,6-(CH₃)₂ | HBr | 190.0 |
| 5-C₄H₉ | HBr | ±125 |
| 4,5-(CH=CH—CH=CH) | — | — |
| 4-C₉H₁₉ | — | — |
| 4-C₄H₉ | — | — |
| 5,6-(CH=CH—CH=CH) | — | 189.3 |
| 6-C(CH₃)₃ | HBr | — |
| 4-CH₃, 7-CH(CH₃)₂ | — | — |
| 6-C₄H₉ | — | — |
| 4-C₂H₅ | HBr | 111.3 |
| 6-C₃H₇ | HBr | — |
| 5-C₅H₉ | — | — |
| 4,7-(CH₃)₂ | HBr | 180.0 |
| 4-CH₃, 7-C(CH₃)₃ | — | — |
| 6-CH₃ | — | 148.4 |
| 4-CH₃, 7-C₄H₉ | — | — |

PREPARATION OF FINAL COMPOUNDS

Example XI

To a stirred and cooled (0° C.) solution of 27.2 parts of 3-[(5-nitro-2-benzothiazolyl)amino]-1-propanol in 135 parts of N,N-dimethylformamide is added dropwise a solution of 15.7 parts of thionyl chloride in 45 parts of N,N-dimethylformamide. Upon completion, the whole is heated slowly to 120° C. and stirring at 120° C. is continued for 4 hours. The reaction mixture is cooled and the precipitated product is filtered off. It is washed with N,N-dimethylformamide and 2,2'-oxybispropane, and dried, yielding 24.4 parts (80%) of 3,4-dihydro-7-nitro-2H-pyrimido[2,1-b]benzothiazole monohydrochloride; mp. 328°–339° C.

Following the same procedure and using equivalent amounts of the appropriate starting materials there are also prepared:

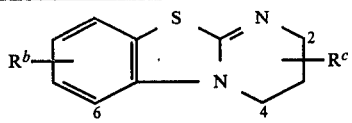

| $R^c$ | $R^b$ | Salt/base | Melting Point in °C. |
|---|---|---|---|
| 3-$C_6H_5$ | 7-$NO_2$ | — | 166.1 |
| — | 7-CO—$C_6H_5$ | HCl | 283–285 |
| — | 6,7-$(CH_2)_4$ | HCl | +300° |
| — | 8-$C_2H_5$ | — | 79.7 |
| — | 6-$CH_3$ | HCl | 298.0 |
| — | 6-$C_3H_7$ | HCl | 230.9 |
| — | 7-$CH_3$ | HCl | 313–335 |
| — | 8-$CH(CH_3)_2$ | $(COOH)_2$ | 130.5 |
| — | 7,8-$(CH_3)_2$ | HCl | +300 |
| — | 7-$C_4H_9$ | HCl | 228.7 |
| — | 6,7-(CH=CH—CH=CH) | HCl | +300 |
| — | 6-$C_9H_{19}$ | HCl | 181.4 |
| — | 6-$C_4H_9$ | HCl | 203.4 |
| — | 8-$C(CH_3)_3$ | HCl | 225.5 |
| — | 6-$CH_3$, 9-$CH(CH_3)_2$ | — | 145.3 |
| — | 8-$C_4H_9$ | HCl | 141.0 |
| — | 7,8-(CH=CH—CH=CH) | HCl ½$H_2O$ | +300 |
| — | 8-$C_3H_7$ | (E)1 ½HOOC—CH=CH—COOH | 170.4 |
| — | 6-$C_2H_5$ | HCl | 254.2 |
| — | 7-$C_5H_{11}$ | HCl.$H_2O$ | 196.2 |
| — | 6,9-$(CH_3)_2$ | — | 86.5 |
| — | 6-$CH_3$, 9-$C(CH_3)_2$ | $HNO_3$ | 231.5 |
| — | 6-$CH_3$, 9-$C_4H_9$ | HCl | 256.7 |
| — | 8-$CH_3$ | HCl | 274.8 |
| — | 7-$C(CH_3)_3$, 9-$NO_2$ | — | 252.6 |
| — | 9-$NO_2$ | — | 268.2 |
| — | 8-c.$C_6H_{13}$ | — | 103.3 |

Example XII

To 92 parts of concentrated sulfuric acid are added portionwise 18.5 parts of 3,4-dihydro-2H-pyrimido[2,1-b]benzothiazole nitrate at 0° C. Upon completion, stirring is continued for 1 hour without cooling. The reaction mixture is poured onto 200 parts of ice-water and stirred for a while. The whole is alkalized with ammonium hydroxide and the product is extracted with trichloromethane. The extract is dried, filtered and evaporated. The residue is stirred in 2,2'-oxybispropane. The product is filtered off and dried, yielding 16.3 parts of 3,4-dihydro-8-nitro-2H-pyrimido[2,1-b]benzothiazole; mp. 247.6° C.

Following the same procedure and starting from the appropriate nitrate salt there are also prepared:
9-(1,1-dimethylethyl)-3,4-dihydro-6-methyl-8-nitro-2H-pyrimido-[2,1-b]benzothiazole monohydrochloride; mp.>260° C.;
8-ethyl-3,4-dihydro-7-nitro-2H-pyrimido[2,1-b]benzothiazole; mp. 156.2° C.;
3,4-dihydro-7,8-dinitro-2H-pyrimido[2,1-b]benzothiazole; mp. 207.4° C.; and
3,4-dihydro-8-methyl-7-nitro-2H-pyrimido[2,1-b]benzothiazole; mp. 204° C.

Example XIII

A mixture of 14 parts of 3,4-dihydro-8-nitro-2H-pyrimido[2,1-b]benzothiazole and 400 parts of methanol, saturated with ammonia is hydrogenated at normal pressure and at room temperature with 5 parts of platinum-on-charcoal catalyst 5%. After the calculated amount of hydrogen is taken up, the catalyst is filtered off and the filtrate is evaporated. The residue is crystallized from 2-propanol. The product is filtered off and dried, yielding 9.3 parts of 3,4-dihydro-2H-pyrimido[2,1-b]benzothiazol-8-amine; mp. 186.5° C.

In a similar manner there is also prepared:
9-(1,1-dimethylethyl)-3,4-dihydro-6-methyl-2H-pyrimido[2,1-b]benzothiazol-8-amine; mp. 238° C.

Example XIV

A mixture of 18 parts of 3,4-dihydro-7-nitro-2H-pyrimido[2,1-b]benzothiazole and 240 parts of methanol, previously saturated with gaseous ammonia is hydrogenated at normal pressure and at room temperature with 5 parts of palladium-on-charcoal catalyst 5%. After the calculated amount of hydrogen is taken up, the catalyst is filtered off and the filtrate is evaporated. The residue is crystallized from 4-methyl-2-pentanone. The product is filtered off and dried, yielding 8.6 parts of 3,4-dihydro-2H-pyrimido[2,1-b]benzothiazol-7-amine; mp. 197° C.

In a similar manner there is also prepared:
3,4-dihydro-3-phenyl-2H-pyrimido[2,1-b]benzothiazol-7-amine; mp. 186.6° C.

Example XV

A mixture of 5.26 parts of 8-ethyl-3,4-dihydro-7-nitro-2H-pyrimido[2,1-b]benzothiazole and 100 parts of acetic acid is hydrogenated at normal pressure and at room temperature with 1 part of platinum-on-charcoal catalyst 5%. After the calculated amount of hydrogen is taken up, the catalyst is filtered off and the filtrate is acidified with 2-propanol, saturated with gaseous hydrogen chloride. The precipitated product is filtered off and dissolved in 200 parts of water. The solution is alkalized with ammonium hydroxide. The precipitated product is filtered off, washed with water and crystallized from 2-propanol, yielding 2.2 parts of 8-ethyl-3,4-dihydro-2H-pyrimido[2,1-b]benzothiazol-7-amine; mp. 209.9° C.

In a similar manner there are also prepared:
7-(1,1-dimethylethyl)-3,4-dihydro-2H-pyrimido[2,1-b]benzothiazol-9-amine as a residue;
3,4-dihydro-2H-pyrimido[2,1-b]benzothiazol-9-amine dihydrochloride; mp. +300° C. and
3,4-dihydro-8-methyl-2H-pyrimido[2,1-b]benzothiazol-7-amine; mp. 245° C.

Example XVI

A mixture of 5.13 parts of 3,4-dihydro-2H-pyrimido[2,1-b]benzothiazol-7-amine and 6.5 parts of diethyl 2-(ethoxymethylene)propanedioate is stirred for 30 minutes at 100°–110° C. The product solidifies on triturating in 1,1'-oxybisethane, yielding 9 parts (96%) of diethyl 2-[(3,4-dihydro-2H-pyrimido[2,1-b]benzothiazol-7-yl)aminomethylene]propanedioate.

By reacting the appropriate primary amine with 2-(ethoxymethylene)propanedioate following the same procedure there are also prepared:
diethyl 2-[3,4-dihydro-2H-pyrimido[2,1-b]benzothiazol-8-yl)aminomethylene]propanedioate; mp. 159.7° C.;
diethyl 2-[(8-ethyl-3,4-dihydro-2H-pyrimido[2,1-b]benzothiazol-7-yl)aminomethylene]propanedioate; mp. 163.4° C.;
diethyl 2-{[7-(1,1-dimethylethyl)-3,4-dihydro-2H-pyrimido[2,1-b]benzothiazol-9ylamino]methylene}propanedioate; mp. 176.4° C.;
diethyl 2-[(3,4-dihydro-2H-pyrimido[2,1-b]benzothiazol-9-ylamino)methylene]propanedioate; mp. 149.2° C.; and
diethyl 2-[(3-dihydro-8-methyl-2H-pyrimido[2,1-b]benzothiazol-7-ylamino)methylene]propanedioate; mp. 182.5° C.

Example XVII

To a stirred solution of 9 parts of diethyl 2-[(3,4-dihydro-2H-pyrimido[2,1-b]benzothiazol-7-yl)aminomethylene]propanedioate in 100 parts of hexamethylphosphoric triamide are added portionwise 1.13 parts of sodium hydride dispersion 74.8% (exothermic reaction: temp. rises to 30° C.). After stirring for one hour, 6.4 parts of dipropyl sulfate are added dropwise (slightly exothermic reaction: temp. rises from 22° to 28° C.). Upon completion, stirring is continued for 5 hours at 40° C. 540 Parts of methylbenzene are added and the organic phase is washed three times with water, dried, filtered and evaporated, yielding 12 parts of diethyl 2-{[(3,4-dihydro-2H-pyrimido[2,1-b]benzothiazol-7-yl)propylamino]methylene}propanedioate as a residue.

In a similar manner there are also prepared:
diethyl 2-{[(3,4-dihydro-2H-pyrimido[2,1-b]benzothiazol-7-yl)methylamino]methylene}-propanedioate; mp. 166.2° C.;
diethyl 2-{[(3,4-dihydro-2H-pyrimido[2,1-b]benzothiazol-7-yl)ethylamino]methylene}propanedioate; mp. 149.3° C.;
diethyl 2-{[(3,4-dihydro-2H-pyrimido[2,1-b]benzothiazol-8-yl)ethylamino]methylene}propanedioate as a residue;
diethyl 2-[(3,4-dihydro-2H-pyrimido[2,1-b]benzothiazol-7-yl)-(2-propenyl)aminomethylene]propanedioate as a residue;
diethyl 2-[ethyl-(8-ethyl-3,4-dihydro-2H-pyrimido[2,1-b]benzothiazol-7-yl)amino]methylene-propanedioate as a residue;
diethyl 2-[{[7-(1,1-dimethylethyl)-3,4-dihydro-2H-pyrimido[2,1-b]benzothiazol-9-yl]ethylamino}methylene]propanedioate as a residue;
diethyl 2-{[(3,4-dihydro-2H-pyrimido[2,1-b]benzothiazol-9-yl)ethylamino]methylene}propanedioate as a residue; and
diethyl 2-{[(3,4-dihydro-8-methyl-2H-pyrimido[2,1-b]benzothiazol-7-yl)propylamino]methylene}propanedioate as a residue.

Example XVIII

A mixture of 3 parts of diethyl 2-{[(3,4-dihydro-2H-pyrimido[2,1-b]benzothiazol-7-yl)methylamino]methylene}-propanedioate, 18 parts of a concentrated hydrochloric acid and 15 parts of water is stirred and refluxed for 30 minutes. The reaction mixture is cooled and alkalized with ammonium hydroxide. After stirring for a while, the precipitated product is filtered off, washed with water and dried, yielding 1.5 parts of 3,4-dihydro-N-methyl-2H-pyrimido[2,1-b]benzothiazol-7-amine; mp. 184.1° C.

Following the same hydrolysis-procedure there are also prepared:
3,4-dihydro-N-propyl-2H-pyrimido[2,1-b]benzothiazol-7-amine; mp. 115°–120° C.;
N-ethyl-3,4-dihydro-2H-pyrimido[2,1-b]benzothiazol-7-amine; mp. 154.8° C.;
N-ethyl-3,4-dihydro-2H-pyrimido[2,1-b]benzothiazol-8-amine; mp. 203.2° C.;
3,4-dihydro-N-(2-propenyl)-2H-pyrimido[2,1-b]benzothiazol-7-amine; mp. 125.3° C.;
N,8-diethyl-3,4-dihydro-2H-pyrimido[2,1-b]benzothiazol-7-amine; mp. 159.4° C.;
7-(1,1-dimethylethyl)-N-ethyl-3,4-dihydro-2H-pyrimido[2,1-b]benzothiazol-9-amine; mp. 180.1° C.;
N-ethyl-3,4-dihydro-2H-pyrimido[2,1-b]benzothiazol-9-amine; mp. 129.5° C.; and
3,4-dihydro-8-methyl-N-propyl-2H-pyrimido[2,1-b]benzothiazol-7-amine; mp. 137.7° C.

Example XIX

A mixture of 3 parts of 3,4-dihydro-2H-pyrimido[2,1-b]benzothiazol-7-amine, 1.6 parts of 3-pentanone and 30 parts of acetic acid is stirred for 10 minutes at room temperature. Then there is added portionwise 1 part of sodium borohydride at a temperature between 18°–20° C. (cooling is necessary). Upon completion, stirring is continued for 20 minutes at room temperature. The reaction mixture is alkalized to pH 8–9 with ammonium hydroxide while cooling. The product is extracted with trichloromethane. The aqueous phase is separated and extracted with trichloromethane. The combined organic phases are washed with water, dried, filtered and evaporated. The residue is purified by column-chromatography over silica gel using a mixture of trichloromethane and methanol (95:5 by volume), saturated with ammonia, as eluent. The pure fractions are collected and the eluent is evaporated. The residue is crystallized from 2,2'-oxybispropane. The product is filtered off and dried, yielding 2.2 parts of N-(1-ethylpropyl)-3,4-dihydro-2H-pyrimido[2,1-b]benzothiazol-7-amine; mp. 114.4° C.

By reacting an appropriate primary amine with an appropriate ketone or aldehyde there are also prepared:

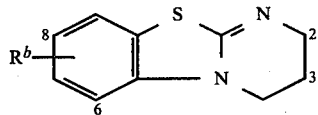

| $R^b$ | Salt or base | Melting point in °C. |
|---|---|---|
| 8-NH—c.C$_5$H$_{11}$ | — | 138.4 |
| 8-NH—CH(C$_2$H$_5$)$_2$ | — | 136.6 |
| 7-NH—CH$_2$C(CH$_3$)$_3$ | — | 174.3 |
| 7-NH—CH$_2$—C$_6$H$_5$ | — | 151.1 |
| 7-NH—CH(CH$_3$)C$_4$H$_9$ | — | 97.9 |
| 7-NH—c.C$_5$H$_{11}$ | — | 169.3 |
| 7-NH—CH(CH$_3$)$_2$ | — | 137.3 |
| 7-NH—CH(CH$_3$)C$_2$H$_5$ | — | 103.0 |
| 7-NH—CH$_2$—(4-OCH$_3$—C$_6$H$_4$) | — | 135.3 |
| 8-NH—CH(CH$_3$)CH(CH$_3$)$_2$ | — | 113.9 |
| 8-NH—CH$_2$C(CH$_3$)$_3$ | — | 148.6 |
| 8-NH—CH$_2$—(4-CH$_3$—C$_6$H$_4$) | — | 166.0 |
| 8-NH—CH$_2$—[3,4,5-(OCH$_3$)$_3$C$_6$H$_2$] | HCl | 190.4 |
| 8-NH—CH(CH$_3$)$_2$ | — | 133.1 |
| 6-CH$_3$, 8-NH—CH(CH$_3$)$_2$, 9-C(CH$_3$)$_3$ | — | 174.6 |
| 7-NH—CH(CH$_3$)CH$_2$OCH$_3$ | — | 103.0 |
| 7-NH—CH(CH$_3$)CH$_2$OH | — | 222.3 |
| 7-NH—CH(CH$_3$)CH$_2$OCH$_2$C$_6$H$_5$ | — | 172.2 |
| 7-NH—CH(CH$_3$)$_2$, 8-C$_2$H$_5$ | — | 109.2 |
| 7-NH—c.C$_5$H$_{11}$, 8-C$_2$H$_5$ | — | 108.9 |
| 7-NH—CH(C$_2$H$_5$)$_2$, 8-C$_2$H$_5$ | 2 HCl.2H$_2$O | 197.0 |
| 7-C(CH$_3$)$_3$, 9-NHCH(CH$_3$)$_2$ | — | 206.0 |
| 9-NH—CH(CH$_3$)$_2$ | — | 150.2 |

Example XX

To a stirred mixture of 45 parts of trifluoroacetic acid and 2 parts of 3,4-dihydro-2H-pyrimido[2,1-b]benzothiazol-7-amine are added portionwise, during a 4 hours-period, 3 parts of sodium borohydride at 30°-40° C. while nitrogen gas is introduced. The reaction mixture is poured onto ice-water and the whole is alkalized with ammonium hydroxide. The product is extracted with methylbenzene. The extract is washed with water, dried, filtered and evaporated. The residue is crystallized from 8 parts of acetonitrile, yielding 0.55 parts of 3,4-dihydro-N-(2,2,2-trifluoroethyl)-2H-pyrimido[2,1-b]benzothiazol-7-amine; mp. 186.7° C.

Example XXI

To 25 parts of acetic acid anhydride are added portionwise 1.3 parts of 3,4-dihydro-2H-pyrimido[2,1-b]benzothiazol-7-amine (exothermic reaction: temp. rises to 30° C.). Upon completion, stirring is continued for one hour at room temperature. After cooling to 5°-10° C., the precipitated product is filtered off and dissolved in water. The solution is treated with activated charcoal. The latter is filtered off over hyflo and the filtrate is alkalized with a few drops of ammonium hydroxide. Upon stirring, the product is allowed to crystallize. It is filtered off and dried, yielding 0.8 parts of N-(3,4-dihydro-2H-pyrimido[2,1-b]benzothiazol-7-yl)acetamide; mp. 178° C.

Example XXII

To a stirred solution of 3 parts of 3,4-dihydro-2-H-pyrimido[2,1-b]benzothiazol-7-amine in 16 parts of acetic acid are added 32 parts of water. Then there is added dropwise a solution of 1.46 parts of potassium cyanate in 32 parts of water (slightly exothermic reaction). Upon completion, stirring is continued overnight at room temperature. The reaction mixture is alkalized with ammonium hydroxide and the whole is stirred while cooling at 10° C. The precipitated product is filtered off and crystallized twice: first from 2-methoxyethanol and then from 1-butanol, yielding 0.6 parts of N-(3,4-dihydro-2H-pyrimido[2,1-b]benzothiazol-7-yl)urea; mp. 245.9° C.

Example XXIII

To a stirred mixture of 2.4 parts of 3,4-dihydro-2H-pyrimido[2,1-b]benzothiazol-7-amine and 100 parts of water are added dropwise 3.44 parts of (1-methylethyl) carbonochloridate. Upon completion, stirring is continued for 24 hours at room temperature. The precipitated product is filtered off and crystallized from 2-propanol, yielding, after drying, 2.4 parts of (1-methylethyl)[(3,4-dihydro-2H-pyrimido[2,1-b]benzothiazol-7-yl)(1-methylethoxycarbonyl)]carbamate monohydrochloride hemihydrate; mp. 170° C.

Example XXIV

A mixture of 1.9 parts of 3,4-dihydro-6-nonyl-2H-pyrimido[2,1-b]benzothiazole, 3.4 parts of 1,3-dichloro-2-(chloromethyl)benzene and 24 parts of acetonitrile is stirred and refluxed for 8 hours. The reaction mixture is evaporated and the residue is crystallized from 4-methyl-2-pentanone. The product is filtered off and dried, yielding 2.8 parts of 1-(2,6-dichlorophenylmethyl)-3,4-dihydro-6-nonyl-2H-pyrimido[2,1-b]benzothiazolium chloride; mp. 174.6° C.

In a similar manner there are also prepared:

3,4-dihydro-1-methyl-6-nonyl-2H-pyrimido[2,1-b]benzothiazolium bromide; mp. 153.7° C.;

3,4-dihydro-6-nonyl-1-(2-propenyl)-2H-pyrimido[2,1-b]benzothiazolium bromide; mp. 151.9° C.;

1-ethyl-3,4-dihydro-7-[(1-methylethyl)amino]-2H-pyrimido[2,1-b]benzothiazolium iodide; mp. 197.7° C.; and 1-ethyl-9-(ethylamino)-3,4-dihydro-2H-pyrimido[2,1-b]benzothiazolium monoiodide; mp. 163.8° C.

Example XXV

To a stirred mixture of 6.2 parts of 3,4-dihydro-2H-pyrimido[2,1-b]benzothiazol-7-amine, 7.8 parts of 3,4,5-trimethoxybenzaldehyde and 60 parts of acetic acid are added portionwise 1.2 parts of sodium borohydride at a temperature between 18° and 20° C. Upon completion, stirring is continued for 30 minutes at room temperature. Water is added and the whole is alkalized with ammonium hydroxide. The product is extracted with trichloromethane. The extract is dried, filtered and evaporated. The residue is crystallized from ethanol, yielding 9.2 parts of 3,4-dihydro-N-(3,4,5-trimethoxyphenylmethyl)-2H-pyrimido[2,1-b]benzothiazol-7-amine; mp. 190.7° C.

In a similar manner there is also prepared:
7-(1,1-dimethylethyl)-3,4-dihydro-N-(3,4,5-trimethoxyphenylmethyl)-2H-pyrimido[2,1-b]benzothiazol-9-amine; mp. 142.9° C.

What is claimed is:

1. A chemical compound selected from the group consisting of 3,4-dihydro-2H-pyrimido[2,1-b]benzothiazoles which may structurally be represented by the formula

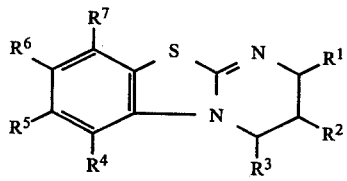

and the pharmaceutically acceptable acid addition salts thereof, and the pyrimido[2,1-b]benzothiazolium salts of formula

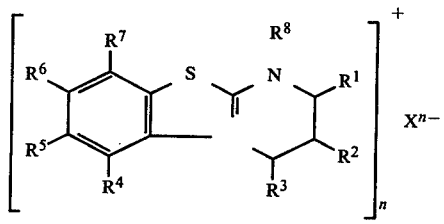

wherein $R^1$, $R^2$ and $R^3$ are each independently selected from the group consisting of hydrogen and aryl;

$R^4$, $R^5$, $R^6$ and $R^7$ are each independently selected from the group consisting of hydrogen, lower alkenyl, lower alkynyl, cycloalkyl, trifluoromethyl-lower alkyl, aroyl, α-hydroxyarylmethyl; nitro and a radical of formula —$NR^9R^{10}$ wherein $R^9$ is a member selected from the group consisting of hydrogen, alkyl, lower alkenyl, lower alkynyl, cycloalkyl, trifluoromethyl-lower alkyl, lower alkanoyl, lower alkyloxycarbonyl, aryllower alkyl, lower alkyloxylower alkyl, aryloxylower alkyl, hydroxy-lower alkyl and aminocarbonyl, and $R^{10}$ is a member selected from the group consisting of hydrogen, alkyl, lower alkanoyl, lower alkyloxycarbonyl and a radical of formula —CH=(COOalkyl)$_2$ or $R^4$ and $R^5$, $R^5$ and $R^6$ or $R^6$ and $R^7$ may form a tri- or tetramethylene bridge or complete a fused benzene nucleus; provided that at least one but no more than two of $R^1$, $R^2$, $R^3$, $R^4$, $R^5$, $R^6$ and $R^7$ is other than hydrogen;

$R^8$ is a member selected from the group consisting of alkyl, lower alkenyl, lower alkynyl and aryllower alkyl;

X is a pharmaceutically acceptable anion; and n represents the valency of the anion;

wherein said aryl is phenyl, optionally substituted with up to 3 substituents, each independently selected from the group consisting of halo, lower alkyl, lower alkyloxy and trifluoro methyl; aroyl is arylcarbonyl; and lower alkanoyl is formyl or lower alkylcarbonyl.

2. A chemical compound according to claim 1 wherein one of $R^4$, $R^5$, $R^6$ and $R^7$ is selected from the group consisting of a radical of formula —$NR^9R^{10}$ wherein $R^9$ is a member selected from the group consisting of hydrogen, alkyl, lower alkenyl, lower alkynyl, cycloalkyl, trifluoromethyllower alkyl, lower alkanoyl, lower alkyloxycarbonyl, aryllower alkyl, lower alkyloxylower alkyl, aryloxylower alkyl, hydroxylower alkyl and aminocarbonyl, and $R^{10}$ is a member selected from the group consisting of hydrogen, alkyl, lower alkanoyl, lower alkyloxycarbonyl and a radical of formula —CH=C-(COOalkyl)$_2$.

3. A chemical compound according to claim 1 wherein one of $R^4$, $R^5$, $R^6$ and $R^7$ is mono- or dialkyl amino.

4. A chemical compound selected from the group consisting of N-(1-ethylpropyl)-3,4-dihydro-2H-pyrimido[2,1-b]benzothiazol-7-amine, the pharmaceutically acceptable acid addition salts thereof, and the pyrimido[2,1-b]benzothiazolium salts thereof.

* * * * *